United States Patent [19]

Turkel

[11] Patent Number: 5,334,159
[45] Date of Patent: Aug. 2, 1994

[54] THORACENTESIS NEEDLE ASSEMBLY UTILIZING CHECK VALVE

[75] Inventor: David Turkel, Fort Lauderdale, Fla.

[73] Assignee: Symbiosis Corporation, Miami, Fla.

[21] Appl. No.: 860,447

[22] Filed: Mar. 30, 1992

[51] Int. Cl.$^5$ .......................................... A61M 5/178
[52] U.S. Cl. ................................... 604/158; 604/247; 604/264; 604/272; 606/185
[58] Field of Search ........................ 604/26, 27, 30, 31, 604/156-158, 164, 247, 169, 272, 274, 264; 128/753, 754, 752, 766; 606/185

[56] References Cited

U.S. PATENT DOCUMENTS

| | | | |
|---|---|---|---|
| 1,527,291 | 2/1925 | Zorraguin | 604/158 |
| 3,313,299 | 4/1967 | Spademan | 128/214.4 |
| 3,459,183 | 8/1969 | Ring et al. | 128/214.4 |
| 3,542,026 | 11/1970 | Bledsoe | 604/247 |
| 3,906,935 | 9/1975 | Raia et al. | 604/323 |
| 3,977,400 | 8/1976 | Moorhead | 128/214.4 |
| 4,000,739 | 1/1977 | Stevens | 128/214.4 |
| 4,177,814 | 12/1979 | Knepshield et al. | 128/348 |
| 4,233,982 | 11/1980 | Bauer et al. | 128/347 |
| 4,245,635 | 1/1981 | Kontos | 128/214.4 |
| 4,379,458 | 4/1983 | Bauer et al. | 604/264 |
| 4,447,235 | 5/1984 | Clarke | 604/169 |
| 4,500,311 | 2/1985 | Redmond et al. | 604/323 |
| 4,535,773 | 8/1985 | Yoon | 604/51 |
| 4,626,245 | 12/1986 | Weinstein | 604/167 |
| 4,784,156 | 11/1988 | Garg | 128/753 |
| 4,808,168 | 2/1989 | Warring | 604/158 |
| 4,832,044 | 5/1989 | Garg | 128/753 |
| 4,840,184 | 6/1989 | Garg | 128/753 |
| 4,844,087 | 7/1989 | Garg | 128/753 |
| 4,850,373 | 7/1989 | Zatloukal et al. | 128/753 |
| 4,869,717 | 9/1989 | Adair | 604/26 |
| 4,891,044 | 1/1990 | Mitchell | 604/27 |
| 4,917,668 | 4/1990 | Haindl | 604/167 |
| 5,098,388 | 3/1992 | Kulkashi et al. | 604/164 |
| 5,098,394 | 3/1992 | Luther | 604/167 |
| 5,104,381 | 4/1992 | Gresl et al. | 604/164 |
| 5,108,380 | 4/1992 | Herlitze et al. | 604/169 |
| 5,122,122 | 6/1992 | Allgood | 604/169 |
| 5,139,485 | 8/1992 | Smith et al. | 604/26 |
| 5,226,426 | 7/1993 | Youn | 604/169 |
| 5,256,148 | 10/1993 | Smith et al. | 604/158 |

FOREIGN PATENT DOCUMENTS

| | | | |
|---|---|---|---|
| 0405883A3 | 1/1991 | European Pat. Off. | A61B 17/34 |
| 0232600B1 | 4/1991 | European Pat. Off. | A61M 1/00 |
| 7535678 | 4/1975 | France | A61B 17/34 |

OTHER PUBLICATIONS

Vernay Custom Engineered Precision Rubber Components catalog.
Surgical Laparoscopy, chap. 2 pp. 40 & 41, by Talamini and Gadacz.
"Veres Needle in the Pleural Space", Southern Med. Journal vol. 76, No. 11, pp. 1383-1385 (Nov. 1983).

Primary Examiner—C. Fred Rosenbaum
Assistant Examiner—Mark Bockelman
Attorney, Agent, or Firm—David P. Gordon

[57] ABSTRACT

A thoracentesis needle assembly is provided and generally comprises a longitudinally extending hollow needle which is sharp at its distal end, a longitudinally extending hollow probe which extends through the hollow needle and has a blunt distal end with an opening, a spring which is coupled to the probe and which resiliently biases the probe forward with respect to the hollow needle such that the blunt distal end of the probe extends past the sharp distal end of the needle, a hollow housing which is fixed to the needle and which houses the spring and permits relative movement of the probe relative to the housing, a hollow luer adapter with its distal end coupled to the housing and its proximal end having a luer mating means, the probe, housing and luer adapter providing a flow path for fluid, and an automatic check valve in the fluid flow path, where the automatic check valve permits flow of fluid in a proximal direction, but prevents flow of fluid in a distal direction. The provided thoracentesis needle assembly substantially eliminates lung puncture, and automatically prevents air leakage into the pleural cavity during thoracentesis.

16 Claims, 4 Drawing Sheets

THORACENTESIS NEEDLE ASSEMBLY UTILIZING CHECK VALVE

BACKGROUND OF THE INVENTION

The present invention generally relates to medical instruments. More particularly, the present invention relates to thoracentesis needle devices which are used in the removal of fluid from the pleural cavity and which prevent air entry into the pleural cavity during use.

The thoracentesis procedure involves incising through the chest wall, and inserting a tube or catheter through the chest wall and into the pleural cavity. By providing a negative pressure at the proximal end of the catheter, intrathoracic fluid such as blood, puss, air, and other secretions are removed from the pleural cavity. While removal of the intrathoracic fluid is desirable, at the same time it is imperative for a negative pressure to be maintained in the pleural cavity in order to permit the lungs to remain expanded such that breathing can continue. In order to maintain a negative pressure in the pleural cavity, care must be taken to avoid communication between the pleural cavity and atmospheric pressure, as a passage of air from outside the body into the pleural cavity can collapse the lung; a medical condition known as pneumothorax.

A common manner of conducting a thoracentesis procedure is to make a chest wall incision using a needle. In introducing the needle into the pleural cavity, care must be taken to avoid pushing the needle too far and puncturing the lung, as air from the lung space could escape into the pleural cavity and result in a lung collapse. In such cases it is actually possible to produce a pressure within the pleural cavity which is greater than atmospheric pressure, and cardiac compromise is a possible consequence.

A thoracentesis device which purportedly reduces possibility of lung puncture and reduces pneumothorax due to entry of air into the pleural cavity is proposed in U.S. Pat. No. 4,447,235 to Clarke. The proposed device includes a needle having a drainage opening which extends through a catheter and a through an elongated conduit connected to the catheter. The elongate conduit is provided with a seal and a manual valve. The seal, which is punctured by the needle when the needle is inserted through the elongate conduit and catheter, prevents air leakage into the pleural cavity by sealing around the needle and resealing when the needle is removed. The manual valve, when moved, permits the elongate conduit to open to a side conduit when the needle is removed, thereby permitting long term drainage of the pleural cavity. In the Clarke patent, the removal of the needle is what reduces the possibility of lung puncture.

In addition to the device proposed in the Clarke patent, devices and procedures are set forth in U.S. Pat. Nos. 4,784,156, 4,832,044, 4,840,184, and 4,844,087 to Garg. In the Garg patents, an manual in-line valve is provided, and upon retraction of the needle past the valve, the valve is turned such that entry of air into the pleural cavity is prevented.

While the prior art patents represent advances in the art, it should be appreciated that with the prior art devices, it is still relatively easy for even a skilled surgeon to puncture the lung by pushing the needle just slightly too far into the pleural cavity. In fact, even if the needle is in the pleural cavity for a short period of time, should the patient move or cough, or even take a deep breath, it is possible for the needle to puncture the lung. In addition, with the manual valve structures of the prior art, should the attending surgeon forget to properly move the valve into the desired positions as certain times, undesirable results may be obtained.

Also long known in the art are needles called "Veress" or "Veress-type" needles. Veress needles are needles with an outer needle having a sharp distal end and an inner probe which extends through the outer needle with the probe having a blunt distal end. In Veress needles, the inner probe is biased to force the blunt distal end of the probe beyond the sharp distal end of the outer needle. However, when the blunt distal end of the probe encounters dense material, the probe is forced backward and the sharp end of the needle is presented so that it can puncture the dense material. Veress needles are used in the art almost exclusively for insufflation (injection of air) of the abdomen during laparoscopy procedures, and Veress needles with manual shut-off valves are known in the art. Veress needles have also been suggested for use in a thoracentesis procedure (See, Jenkins, Jr. Douglas, et al., "Veres Nedle in the Pleural Space" *Southern Medical Journal:* Vol 76, No. 11, pp. 1,383–1,385 (November 1983)), although the techniques suggested therein in a test study have not gained popularity over the several years since they were reported and are not today used in common practice. Regardless of use, the Veress needle assemblies of the art have not before been modified for particular use in conjunction with withdrawal of fluid, and in particular withdrawal of fluid from the pleural cavity. Indeed, the Veress needle assemblies of the art have not been used with automatic check valves.

SUMMARY OF THE INVENTION

It is therefore an object of the invention to provide a thoracentesis needle assembly which substantially eliminates lung puncture.

It is another object of the invention to provide a thoracentesis needle assembly which automatically prevents air leakage into the pleural cavity.

It is a further object of the invention to provide a thoracentesis needle assembly having a first needle having a sharp end and a second forwardly biased concentric probe having a blunt end, where the blunt end of the probe extends past the sharp end of the needle when force is not applied to the blunt end of the probe.

An additional object of the invention is to provide a thoracentesis needle assembly which provides visual and/or audible signals to a practitioner when the pleural cavity has been reached.

Yet a further object of the invention is to provide a thoracentesis needle assembly which substantially eliminates lung puncture, automatically prevents air leakage into the pleural cavity, and is easy to use.

Another object of the invention is to provide a thoracentesis needle assembly which substantially eliminates lung puncture and which can be used in conjunction with a catheter for pleural cavity drainage.

In accord with the objects of the invention, a thoracentesis needle assembly is provided and generally comprises a Veress-type needle assembly, a hollow luer adapter with its distal end coupled to the Veress-type needle assembly and its proximal end having a luer mating means, the Veress-type needle assembly and luer adaptor providing a flow path for fluid, and an automatic check valve in the flow path, where the automatic check valve permits flow of fluid in a proximal direction, but prevents flow of fluid in a distal direction. The Veress-type needle assembly preferably includes a longitudinally extending hollow needle which is sharp at its distal end, a longitudinally extending hollow probe which extends through the hollow needle and has a blunt distal end with an opening, a spring which is coupled to the probe and which resiliently biases the probe forward with respect to the hollow needle such that the blunt distal end of the probe extends past the sharp distal end of the needle, and a hollow housing which is fixed to the needle and which houses the spring and permits relative movement of the probe relative to the housing. Any type of automatic check valve may be used, including a duck bill valve, a flapper valve, a ball in socket valve, an umbrella valve, a diaphragm valve, a v-tip needle valve, etc.

In accord with an additional preferred aspect of the invention, a visual indication is provided for indicating to the practitioner when the blunt end of the probe is being forced backward and the sharp end of the needle is incising as opposed to when the blunt end of the probe is extending past the sharp end of the needle. The visual indication is embodied in a red indicator, a green indicator, an opaque shield, and a second opaque shield which is longitudinally spaced from the first opaque shield. The opaque shields are both coupled to the housing. The red indicator is coupled to the probe near its proximal end, and the green indicator is coupled to the probe adjacently proximal the red indicator. The red indicator sits in and is shielded by the first opaque shield when the blunt distal end of the probe extends past the sharp distal end of the needle, and when the red indicator is shielded, the green indicator is seen in the longitudinal gap between the opaque shields. Likewise, when the blunt distal end of the probe is forced backward, the green indicator is shielded by the second opaque shield, and the red indicator is seen in the longitudinal gap between the opaque shields. Preferably, the second opaque shield has means for holding the automatic check valve.

Additional objects and advantages of the invention will become apparent to those skilled in the art upon reference to the detailed description taken in conjunction with the provided figures.

BRIEF DESCRIPTION OF THE DRAWINGS

FIGS. 2a, 2b, and 2c are respectively top, side, and rear views of the housing and the sharp needle of the thoracentesis needle assembly of FIG. 1a.

FIGS. 3a, 3b, and 3c are perspective views respectively of the opaque shield, the first colored indicator, and the second colored indicator of the thoracentesis needle assembly of FIG. 1a.

FIGS. 4a and 4b are respectively front and rear views of the opaque cylinder of FIG. 1a in the planes 4A—4A and 4B—4B of FIG. 1a.

FIGS. 5a and 5b are respectively front and rear views of the luer adapter of FIG. 1a in the planes 5A—5A and 5B—5B of FIG. 1a.

DETAILED DESCRIPTION OF THE PREFERRED EMBODIMENT

Figure 1A:
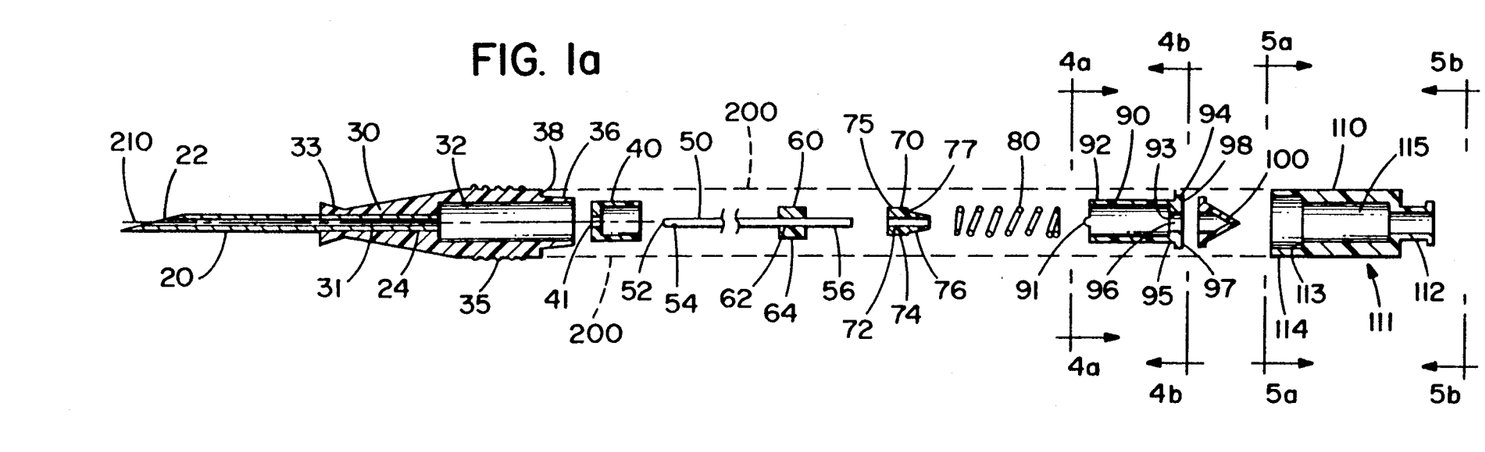
FIG. 1a is an exploded view in cross section of the thoracentesis needle assembly of the invention.
Figure 1B:
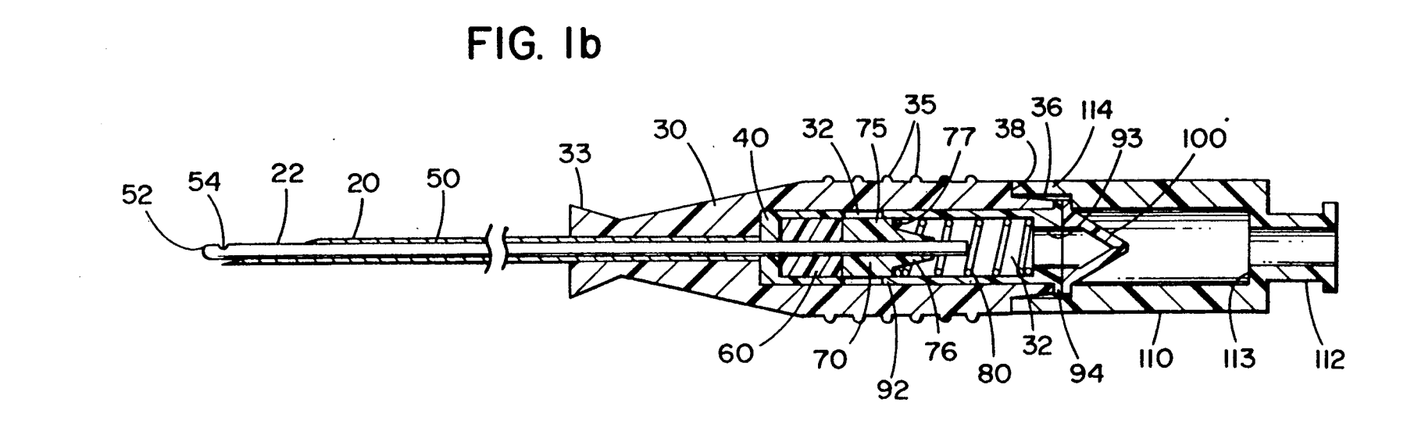
FIG. 1b is a cross section of the thoracentesis needle assembly of FIG. 1a assembled.

Turning to FIGS. 1a and 1b, the preferred thoracentesis needle assembly 10 of the invention is seen. The preferred thoracentesis needle assembly 10 of the invention is comprised of ten parts, including: a longitudinally extending hollow needle 20, a hollow housing 30, an opaque shield 40, a hollow probe 50, a red indicator 60, a green indicator 70, a spring 80, an opaque cylinder 90, an automatic check valve 100, and a luer adapter 110. Together, the needle 20, housing 30, probe 50, and spring 80 constitute a Veress-type needle assembly. In fact, those four pieces with a modified housing, together with the the opaque shield 40, indicators 60 and 70, and an opaque cylinder modified from the opaque cylinder 90 are manufactured as a Veress needle assembly by the assignee of this invention.

Figure 2A:
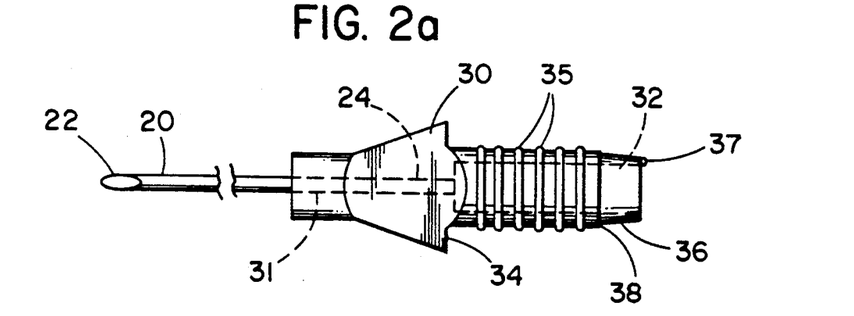
Figure 2B:
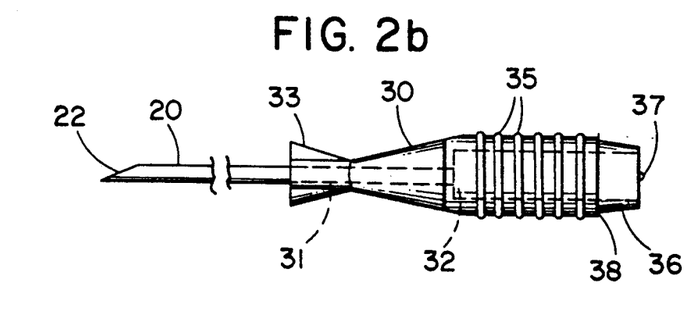
Figure 2C:
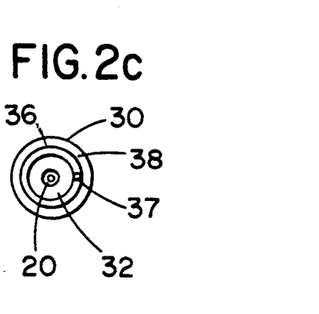

Turning to FIGS. 2a-2c in conjunction with FIGS. 1a and 1b, it is seen that the hollow needle 20 has a sharp distal end 22 and a proximal end 24. In manufacture, the hollow needle 20 is preferably insert molded into the housing 30 such that the proximal end 24 of the needle is held in the housing and effectively integral with the housing 30 as seen in FIG. 1a. Thus, the housing 30 is provided with a passage 31 in which the needle is held. Passage 31 opens up into a cylindrical chamber 32 which is sized to receive the opaque shield 40 and cylinder 90 as discussed hereinafter. The outer surface of housing 30 is preferably provided with flanges 33 and 34, ribs 35, and a tapering rear portion 36 with a locator nub 37 at its proximal end, and an abutment surface 38. The ribs 35 are provided as finger grips, while flanges 33 and 34 are provided to prevent the practitioner's hand from sliding off of the housing 30 should the practitioner lose grip when applying force to the housing 30. The tapering rear portion 36 and abutment surface 38 are provided as a mating surface for the luer adapter 110 as indicated by the lineup lines 200 and as discussed hereinafter, while the locator hub 37 is provided for aligning and preventing rotation of the opaque cylinder 90 as discussed hereinafter.

Figure 3A:
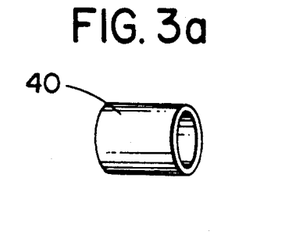

The cylindrical chamber 32 of the housing 30 receives the opaque shield 40. The opaque shield 40 seen in FIG. 3a is preferably formed of opaque plastic and has an outer diameter just slightly smaller than the inner diameter of the cylindrical chamber. Thus, the opaque shield 40 is slid into place in the cylindrical chamber 32 and sits therein. The opaque shield 40 is substantially cylindrical and hollow, and as seen in FIG. 1a includes an opening or hole 41 in its distal end in which the proximal end 24 of the hollow needle 20 terminates.

The hollow probe 50 may be a standard Veress-type needle probe having a blunt distal end 52 with one or more ports or openings 54, and a proximal end 56. Because the distal end 52 of the hollow probe is blunt, it is preferably closed. The opening(s) 54 in the distal end 52 are thus provided to permit fluid to enter the probe from outside the probe, e.g., the pleural cavity. As shown in FIG. 1a, the openings 54 in the distal end 52 of the probe are formed as radial slots which are parallel the longitudinal axis of the probe. As indicated by guide line 210, the probe is inserted through the opaque shield 40, the housing 30, and through the needle 20. The probe 50, however, is preferably longer than the sharp ended needle 20 such that, seen in FIG. 1b, the blunt distal end 52 of the probe 50 extends past the sharp distal end 22 of the needle 20 while the proximal end 56 of the probe extends into chamber 32 of housing 30.

Figure 9:
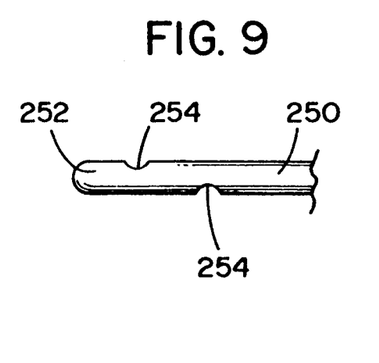
FIG. 9 is a side elevational view of a modified probe for the thoracentesis needle assembly of the invention.

Turning to FIG. 9, an alternative and preferred probe 250 is seen for use in the thoracentesis needle assembly 10. Probe 250 is provided with a plurality of ports or openings 254 which are on opposite sides of the probe 250 and which are offset longitudinally. The longitudinal offset of the ports strengthens the probe, and permits the use of a smaller gauge needle.

Figure 3B:
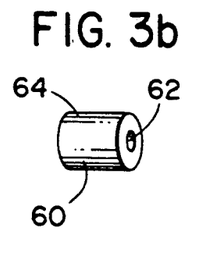
Figure 3C:
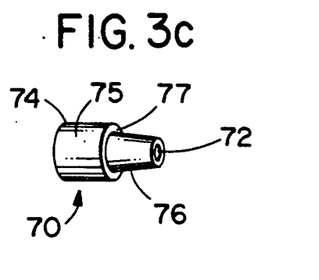

Turning to FIGS. 3b and 3c, differently colored indicators 60 and 70 are seen. Colored indicator 60 is preferably a red or pink plastic cylinder having an axial passage 62 through which the proximal end 56 of the probe 50 extends. The outer surface 64 of the red indicator 60 is sized such that the red indicator 60 fits into opaque shield 40; i.e., the outer diameter of red indicator 60 is slightly smaller than the inner diameter of opaque shield 40, and the length of red indicator 60 is slightly smaller than the length of opaque shield 40. As suggested by FIG. 1a, the red indicator 60 is preferably affixed to the probe 50 such as by gluing or other fastening means.

Colored indicator 70 is preferably formed of green plastic. Green indicator 70 has an axial passage 72 through which the proximal end 56 of the probe extends. The outer surface 74 of the green indicator preferably includes a distal cylindrical portion 75 having an outer diameter equal to the outer diameter of the red indicator 60, and a proximal frusto-conical portion 76 with an outer diameter less than the outer diameter of the cylindrical portion. Where the cylindrical portion 75 and frusto-conical portion 76 meet, a seat 77 is formed. The surface of the frusto-conical portion 76 and the seat 77 provide a centering mechanism and stop for the spring 80.

Figure 4A:
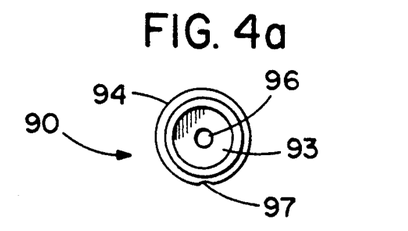
Figure 4B:
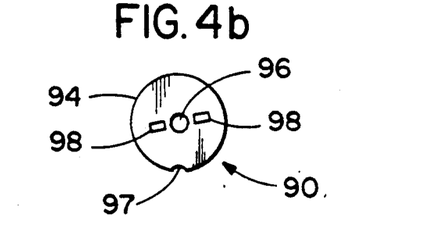

The opaque cylinder 90 seen in FIGS. 4a and 4b is preferably formed of opaque plastic and is substantially a hollow cylinder. The opaque cylinder 90 has hubs 91 extended from its open distal end 92, an inwardly extending seat 93 and an outwardly extending flange 94 located toward its proximal end 95, a hole 96 in the seat in the proximal end 95, a locator notch 97 in the flange 94, and valve holding arms 98 extending from the rear surface of the seat 93. Most of the opaque cylinder 90 sits in the chamber 32 of the housing 30, and the opaque cylinder 90 has several functions. First, the opaque cylinder acts as an opaque shield for the green indicator 80 when the probe 50 is pushed backward relative to the needle 20 as discussed hereinafter. Thus, the distal end 92 of the opaque cylinder has an inner diameter greater than the outer diameter of the indicators 80. However, in order to avoid shielding both the green and red indicators from view, the opaque cylinder 90 is provided with the nubs 91 which provide an axial offset relative to the opaque shield 40. Second, the opaque cylinder 90 provides a housing for and a stop for the spring 80. Spring 80 is held between the inwardly extending seat 93 of the opaque cylinder 90 and the seat 77 on the green indicator 70, thereby effectively acting to bias the probe in a forward position relative to the needle. While the green indicator 70 moves with the probe 50 and relative to the housing 30, the opaque cylinder 90 is fixed relative to the housing 30. Thus, when probe 50 is forced backward, the spring 80 is compressed between the seats 77 and 93. When force is no longer applied to the distal end of the probe 50, the spring 80 forces the probe 50 outward past the sharp end of the needle 20. In order to fix the opaque cylinder 90 relative to the housing, the outwardly extending flange 94 sits and may be fixed, if desired, on the proximal edge surface of the tapered portion 36 of the housing with nub 37 of the housing 30 sitting in the locator notch 97 of the flange 94. The mating of the locator notch 97 and the nub 37 are provided to prevent the the opaque cylinder 90 from rotating relative to the housing. Fixing of the flange 94 on the housing 30 is not absolutely necessary, because the luer adapter 110 which is fixed to the housing 30 holds the opaque cylinder 90 in place as hereinafter described.

A third function of the opaque cylinder 90 is to provide a connection mechanism for the automatic check valve 100 of the invention. In the preferred embodiment, a duck billed automatic valve is utilized, and the arms 98 are provided to hold the distal end of the duck billed valve in place.

With all its functions, it should be appreciated that the opaque cylinder 90 still permits fluid to flow therethrough, as the hole 96 is provided in its proximal end. The hole 96 is preferably large enough to permit the proximal end 56 of the hollow probe 50 to extend therethrough, as this would eliminate the need for tight tolerances on the length of the probe 50.

Figure 5A:
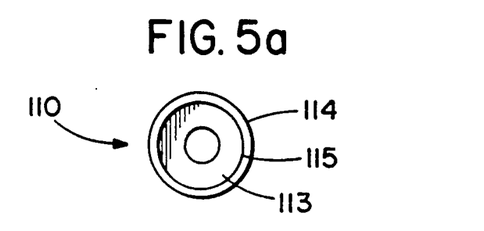
Figure 5B:
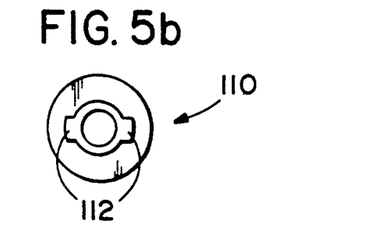

As seen in FIGS. 1a, 5a and 5b, the hollow luer adapter 110 of the invention generally comprises a hollow cylinder 111 in fluid communication with a luer slip or luer lock 112 on its proximal end. The inner surface of the hollow cylinder 111 includes an inwardly extending seat 113 which effectively separates a slightly larger hollow cylinder portion 114 and a slightly smaller hollow cylinder portion 115. The slightly larger hollow cylinder portion 114 has an inner diameter which is slightly larger than the tapered rear portion 36 of housing 30 so that the hollow cylinder portion 114 slides over and mates therewith with the distal surface of the larger hollow cylinder portion 114 abutting the abutment surface 38 on the housing 30. Preferably, the two are fixed in place by glue or sonic welding. The slightly larger hollow cylinder portion 114 is also sized such that the flange 94 of the opaque cylinder 90 abuts the seat 113 in the luer adapter. Thus, the flange 94 is held in place between the seat 113 of the luer adapter 110, and the proximal end surface of the housing 30.

The proximal end of the luer adapter as shown in FIGS. 1a, 5a, and 5b comprises a luer lock 112 for mating with the end of a syringe type device. It will be appreciated by those skilled in the art that a luer slip could similarly be utilized as well as other means for mating with a mechanism for creating a "negative pressure".

Figure 6A:
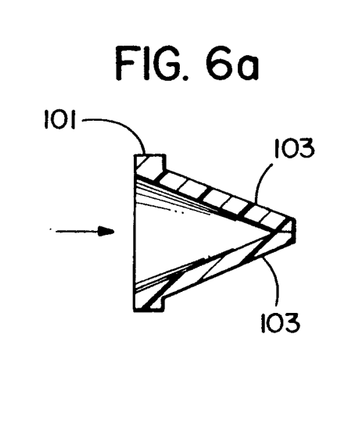
FIGS. 6a, 6b, 6c, 6d, and 6e, are respectively diagrams of a duck bill valve, a flapper valve, a ball in socket valve, an umbrella valve, and a v-tip needle valve.

FIG. 6a shows the duck bill valve 100 as the preferred automatic check valve of the invention. The duck bill check valve 100 is well known in the valve arts, and is typically an elastomeric piece having a round end 101 which tapers into two duck bill shaped portions 103 or flaps which are separated at their ends by a slit. When there is zero or positive pressure forward the flaps relative to the rounded end, the flaps touch and prevent fluid flow through the valve. However, when there is negative pressure forward the flaps relative the rounded end, the flaps open and permit fluid to flow through the valve in the direction from the rounded end to the flaps.

In the embodiment of the invention, the round end 101 of the duck bill check valve 100 fits over and is held by the valve holding arms 98 of the opaque cylinder 90. Thus, the duck bill check valve 100 is an automatic check valve which permits fluid flow only when the pressure at the distal end of the thoracentesis needle assembly 10 is higher than the pressure at the proximal end thereof. As a result, pneumothorax can be effectively avoided.

Figure 6B:
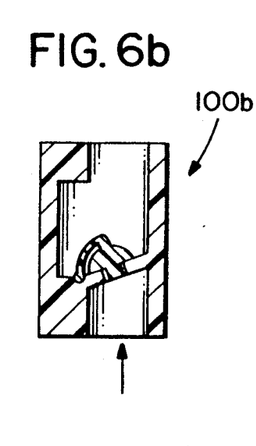
Figure 6C:
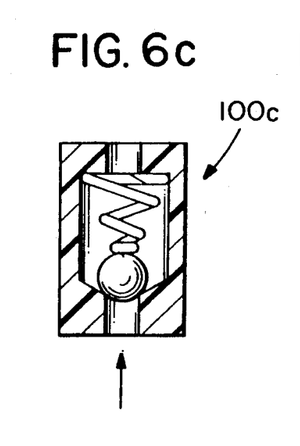
Figure 6D:
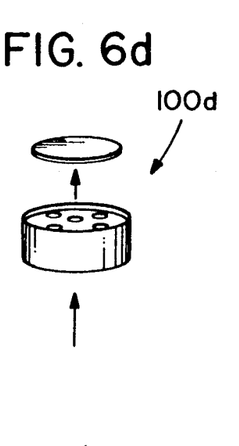
Figure 6E:
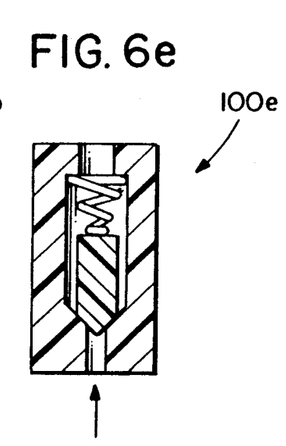

FIGS. 6b, 6c, 6d, and 6e are examples of other automatic check valves which can be utilized in lieu of the duck bill check valve 100. In particular, FIG. 6b shows a flapper check valve 100b; FIG. 6c shows a ball in socket check valve 100c; FIG. 6d shows an umbrella check valve 100d; and FIG. 6e shows a v-tip needle check valve 100e. Of course, other automatic check valves can be utilized. It will be appreciated by those skilled in the art that the use of the automatic check valves of FIGS. 6b–6e or other such automatic check valves may require simple adjustments to the structure of the housing and/or the opaque cylinder and/or the luer adapter. It will also be appreciated that in lieu of an automatic check valve, an automatic valve having a pressure threshold could be utilized, although such an embodiment is not preferred.

The thoracentesis needle assembly 10 of the invention is preferably assembled in the following manner. As aforementioned, the housing 30 is (insert) molded with the sharp needle 20 in place. The red indicator 60 is then slid onto the proximal end of the blunt probe 50 and glued or cemented in place at a predetermined location. The opaque shield 40 is then either inserted into the cylindrical chamber 32 of the housing 30, or is slid over the blunt distal end of probe 50. The green indicator 70 is then slid over the proximal end of probe 50, and the probe 50, with the red 60 and green 70 indicators and possibly the opaque shield 40 thereon is inserted through the housing 30 and through the hollow needle 20 until the shield 40 is in place in the chamber 32 of the housing, with the red indicator 60 in the opaque shield 40 and the blunt end of the probe 50 extending past the sharp end of the needle 20. The spring 80 is then inserted into chamber 32 and on top of the green indicator 70, and the opaque cylinder 90 is placed over spring 80 and arranged such that the locator notch 97 of the opaque cylinder 90 is aligned with the nub 37 of the housing. The duck bill check valve 100 is then placed on the proximal end of the opaque cylinder 90, with the arms 98 of the cylinder holding the valve in place. The luer adapter 110 is placed over the valve 100 and the proximal end of the opaque cylinder 90 such that the flange 94 of the opaque cylinder 90 abuts the seat 113 in the luer adapter, and such that the distal surface of the larger hollow cylinder portion 114 of the luer adapter 110 abuts the abutment surface 38 on the housing 30. The luer adapter 110 is then glued or sonically welded to the housing 30.

Figure 7A:
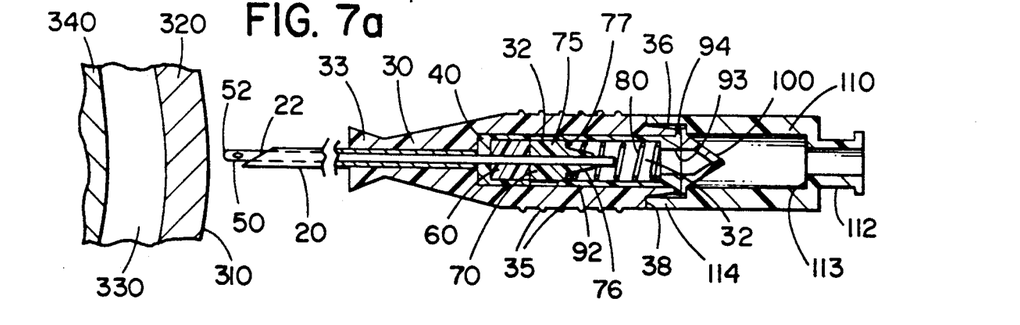
FIGS. 7a, 7b, 7c, and 7d are diagrams showing the thoracentesis needle assembly of FIG. 1a as it progresses from outside the body, to entry into the body, to passing through dense tissue in the body, to entry into the pleural cavity.
Figure 7B:
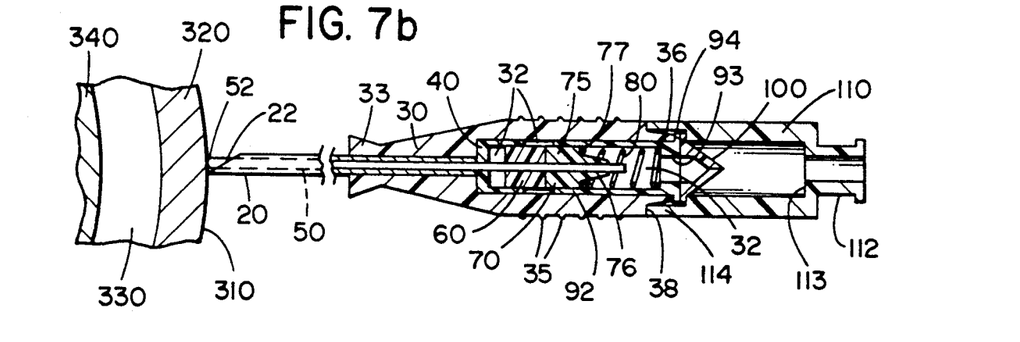
Figure 7C:
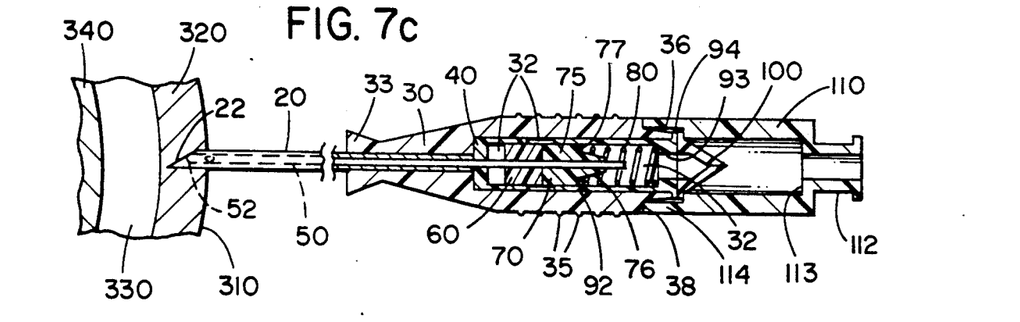
Figure 7D:
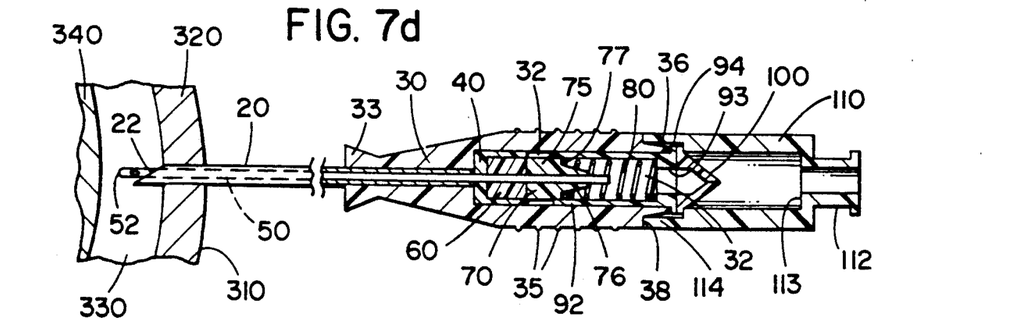

With the thoracentesis needle assembly 10 assembled as described above and sterilized, it may be used in a thoracentesis procedure. In particular, and with reference to FIGS. 7a–7d, in FIG. 7a the thoracentesis needle is seen adjacent the thorax 300 (chest) of an individual with the blunt distal end 52 of probe 50 extending beyond the sharp distal end 22 of needle 20. With the probe 50 extending beyond the needle 20, the green indicator 70 is seen between the opaque shield 40 and the opaque cylinder 90. In FIG. 7b, the thoracentesis needle 10 is pushed up against the skin 310 of the thorax, and the blunt distal end 52 of probe 50 is pushed backward presenting the sharp end 22 of the needle 20. With the probe 50 being pushed backward against the force of the resilient spring 80, the red indicator 60 and green indicator 70 are likewise pushed backward, and the red indicator 60 can be seen between the opaque shield 40 and the opaque cylinder 90, while the green indicator 70 is blocked from view by the opaque cylinder 90. In FIG. 7c, the thoracentesis needle 10 is passing through fascia 320, or dense tissue with the probe 50 pushed backward and the sharp distal end of needle 20 presented. Again, the red indicator 60 is seen between the opaque shield 40 and the opaque cylinder 90. Finally, in FIG. 7d, the distal end of the thoracentesis needle 10 has passed through the dense tissue 320 and is in the pleural cavity 330 separating the dense tissue 320 from the lung 340. Once the thoracentesis needle 10 is in the pleural cavity, the probe 50 is pushed forward by the spring 80 and extends past the sharp distal end of the needle 20. In this position, the green indicator 70 is again seen between the opaque shield 40 and the opaque cylinder 90 and a visual indication is given to the practitioner that no further pushing of the needle is required and that liquid may be obtained by applying a negative pressure to the proximal end of the thoracentesis needle 10. In fact, an audible indication may also be received as the needle 10 enters the pleural cavity 330, as the probe will snap back from its retracted position of FIG. 7c to its extended position of FIG. 7d. With the thoracentesis needle assembly 10 of the invention, the lung 340 is protected from the sharp distal end 22 of the needle 20, as the blunt distal end 52 of probe 50 is presented.

Figure 8:
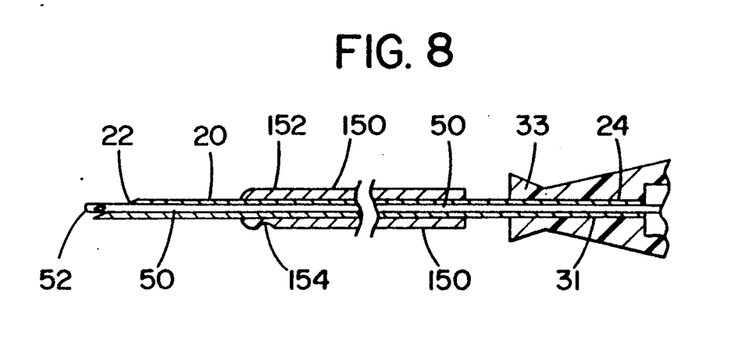
FIG. 8 is a diagrammatic view of a catheter assembly which is useful in conjunction with the thoracentesis needle assembly of the invention.

It will be appreciated by those skilled in the art, that the thoracentesis needle assembly 10 of the invention may be used in conjunction with a catheter, in a manner similar to that disclosed in U.S. Pat. No. 4,447,235 to Clarke which is hereby incorporated by reference herein. Thus, as seen in FIG. 8, a flexible catheter device 150 having a distal end 152 with radial ports or openings 154 is placed over the needle 20. After pleural cavity fluid samples are withdrawn by attachment and activation of a syringe (not shown) to the proximal end of the thoracentesis needle assembly, if it is desirable to drain the cavity, the catheter 150 may be advanced into the cavity, and the thoracentesis needle assembly withdrawn. In order to prevent air from the entering the pleural cavity during this procedure, the catheter 150 may be clamped, or valves such as disclosed in the Clarke patent may be utilized. The proximal end 156 of the catheter 150 is then preferably attached to other flexible tubing (not shown) which terminates at a vacuum bottle (not shown), and the clamp is released to permit drainage.

There have been illustrated and described herein thoracentesis needle assemblies. While particular embodiments of the invention have been described, it is not intended that the invention be limited thereto, as it is intended that the invention be as broad in scope as the art will allow and that the specification be read likewise. Thus, while a spring was disclosed as providing a biasing mechanism for the probe, it will be appreciated that other resilient biasing mechanisms could be utilized. For example, a piece of elastic or rubber (with a hole for fluid communication) could be extend over the rear of the probe and be anchored at a more distal location to provide the forward biasing for the probe. Also, while a particular mechanism was disclosed for providing a visual indication as to when the probe is extended and when it is retracted, it will be appreciated that no visual indicator need be provided, or that other mechanisms for providing a visual indication can be provided. Further, while the preferred parts of the preferred thoracentesis needle assembly of the invention were described as having certain shapes, and being made of certain materials, it will be appreciated that other materials and shapes can be utilized. It will therefore be appreciated by those skilled in the art that yet other modifications could be made to the provided invention without deviating from its spirit and scope as so claimed.

I claim:

1. A thoracentesis needle assembly, comprising:
   a) a longitudinally extending hollow needle having a sharp distal end and a proximal end, and having a longitudinal axis;
   b) a longitudinally extending hollow probe extending through said hollow needle and having a blunt distal end and a proximal end, said probe having at least one port around its distal end;
   c) a resilient biasing means coupled to said longitudinally extending hollow probe for resiliently biasing said probe forward with respect to said hollow needle such that said blunt distal end of said probe extends past said sharp distal end of said needle;
   d) a hollow housing means for housing said resilient biasing means and for permitting relative movement of said probe relative to said hollow housing means, said hollow housing means fixedly coupled to said needle, and said probe and said hollow housing means providing a fluid flow path from said port of said probe to at least a distal end of said hollow housing means;
   e) an automatic check valve means in said fluid flow path, said automatic check valve means for permitting flow of fluid in a direction from said distal end to said proximal end of said probe through said fluid flow path, but preventing flow of fluid in a direction from said proximal end to said distal end of said probe through said fluid flow path; and
   a hollow fluid coupling means having a distal end bonded to said housing means by one of glue and sonic welding, and a proximal end having a fluid coupling mating means, said hollow fluid coupling means further providing said fluid flow path,
   wherein said automatic check valve means is located between said proximal end of said probe and said fluid coupling mating means, and said automatic check valve means permits flow of fluid in a direction from said port of said probe through to said proximal end of said fluid coupling means, but prevents flow of fluid in a direction through said probe from said proximal end of said fluid coupling means through to said port of said probe.

2. A thoracentesis needle assembly according to claim 1, wherein:
   said fluid coupling mating means comprises a luer coupling.

3. A thoracentesis needle assembly according to claim 1, wherein:
   said resilient biasing means comprises a spring coupled to said proximal end of said probe.

4. A thoracentesis needle assembly according to claim 3, further comprising:
   a first indicator having a first color and coupled to said probe near said proximal end of said probe;
   a second indicator having a second color and coupled to said probe adjacent said first indicator near said proximal end of said probe;
   an opaque shield coupled to said hollow housing means, wherein one of said first and second indicators is shielded by said opaque shield when said blunt distal end of said probe extends past said sharp distal end of said needle.

5. A thoracentesis needle assembly according to claim 4, wherein:
   said second indicator has a substantially conical shaped proximal end, and said spring has a distal end and a proximal end, said distal end of said seated on said conical shaped proximal end of said second indicator.

6. A thoracentesis needle assembly according to claim 5, further comprising:
   a cylinder means having a proximal end and a distal end, said cylinder means extending over said resilient biasing means and providing a stop for said distal end of said resilient biasing means, said proximal end having a hole through which said fluid can flow and having valve coupling to and holding means for holding said automatic check valve means, wherein said cylinder means is coupled to said said housing means.

7. A thoracentesis needle assembly according to claim 6, wherein:
   said cylinder means is opaque, and said distal end of said cylinder means is spaced from said opaque shield along said longitudinal axis, whereby said first indicator is shielded by said opaque shield and said second indicator extends between said opaque shield and said opaque cylinder means when said blunt distal end of said probe extends past said sharp distal end of said needle, and said first indicator extends between said opaque shield and said opaque cylinder means and said second indicator is shielded by said opaque cylinder means when said sharp distal end of said needle extends past said blunt distal end of said probe.

8. A thoracentesis needle assembly according to claim 7, wherein:
   said automatic check valve means comprises one of a duck bill valve, a flapper valve, a ball in socket valve, an umbrella valve, and a needle valve.

9. A thoracentesis needle assembly according to claim 2, wherein:
   said resilient biasing means comprises a spring coupled to said proximal end of said probe.

10. A thoracentesis needle assembly according to claim 9, further comprising:
    a first indicator having a first color and coupled to said probe near said proximal end of said probe;
    a second indicator having a second color and coupled to said probe adjacent said first indicator near said proximal end of said probe;
    an opaque shield coupled to said hollow housing means, wherein one of said first and second indicators is shielded by said opaque shield when said blunt distal end of said probe extends past said sharp distal end of said needle.

11. A thoracentesis needle assembly according to claim 10, wherein:

said second indicator has a substantially conical shaped proximal end, and said spring has a distal end and a proximal end, said distal end of said seated on said conical shaped proximal end of said second indicator.

12. A thoracentesis needle assembly according to claim 11, further comprising:

a cylinder means having a proximal end and a distal end, said cylinder means extending over said resilient biasing means and providing a stop for said distal end of said resilient biasing means, said proximal end having a hole through which said fluid can flow and having valve coupling to and holding means for holding said automatic check valve means, wherein said cylinder means is coupled to said housing means.

13. A thoracentesis needle assembly according to claim 12, wherein:

said cylinder means is opaque, and said distal end of said cylinder means is spaced from said opaque shield along said longitudinal axis, whereby said first indicator is shielded by said opaque shield and said second indicator extends between said opaque shield and said opaque cylinder means when said blunt distal end of said probe extends past said sharp distal end of said needle, and said first indicator extends between said opaque shield and said opaque cylinder means and said second indicator is shielded by said opaque cylinder means when said sharp distal end of said needle extends past said blunt distal end of said probe.

14. A thoracentesis needle assembly according to claim 13, wherein:

said automatic check valve means comprises one of a duck bill valve, a flapper valve, a ball in socket valve, an umbrella valve, and a needle valve.

15. A thoracentesis needle assembly according to claim 1, wherein:

said automatic check valve means comprises one of a duck bill valve, a flapper valve, a ball in socket valve, an umbrella valve, and a needle valve.

16. A thoracentesis needle assembly according to claim 1, wherein:

said at least one port comprises at least two ports with a first port on a first side of said probe, and a second port on a side opposite said first side of said probe, wherein said first and second ports are offset longitudinally from each other.

* * * * *